United States Patent
Cornet et al.

(10) Patent No.: US 8,623,047 B2
(45) Date of Patent: Jan. 7, 2014

(54) SYSTEM AND METHOD FOR SEALING AN INCISIONAL WOUND

(75) Inventors: Douglas A. Cornet, San Antonio, TX (US); Michael Manwaring, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 350 days.

(21) Appl. No.: 13/095,384

(22) Filed: Apr. 27, 2011

(65) Prior Publication Data
US 2011/0270301 A1    Nov. 3, 2011

Related U.S. Application Data

(60) Provisional application No. 61/329,764, filed on Apr. 30, 2010.

(51) Int. Cl.
*A61B 17/08* (2006.01)
*A61M 27/00* (2006.01)

(52) U.S. Cl.
USPC .......................................... 606/216; 604/543

(58) Field of Classification Search
USPC ........... 606/213, 215–218; 604/313, 543, 290
See application file for complete search history.

(56) References Cited

U.S. PATENT DOCUMENTS

| | | |
|---|---|---|
| 1,195,430 A | 8/1916 | Angier |
| 1,355,846 A | 10/1920 | Rannells |
| 1,845,630 A | 2/1932 | Scholl |
| 2,452,345 A | 10/1948 | Anselnno |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,026,874 A | 3/1962 | Stevens |
| 3,066,672 A | 12/1962 | Crosby, Jr. et al. |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

International Search Report and Written Opinion date mailed Aug. 30, 2011 for PCT International Application No. PCT/US2011/034300.

(Continued)

*Primary Examiner* — Julian W Woo

(57) ABSTRACT

An apparatus, system, and method for treating an incisional wound having incisional walls is disclosed. The apparatus includes a conduit having a first end for receiving reduced pressure and a second end. The apparatus further includes a scaffold. The scaffold has opposing surfaces for positioning adjacent the incisional walls and is fluidly coupled to the second end of the conduit for receiving the reduced pressure. The scaffold is generally elongated in shape and has a thickness between the opposing surfaces that is sufficiently thin for positioning within the incisional wound. The apparatus further includes an internal manifold that has a primary flow channel extending generally longitudinally within the scaffold and between the opposing surfaces of the scaffold. The internal manifold is fluidly coupled to the second end of the conduit. The application of the reduced pressure through the scaffold and the internal manifold induces tissue apposition between the incisional walls.

55 Claims, 4 Drawing Sheets

(56) References Cited

U.S. PATENT DOCUMENTS

| | | |
|---|---|---|
| 3,367,332 A | 2/1968 | Groves |
| 3,419,006 A | 12/1968 | King |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,892,229 A | 7/1975 | Taylor et al. |
| 4,080,970 A | 3/1978 | Miller |
| 4,091,804 A | 5/1978 | Hasty |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,224,945 A | 9/1980 | Cohen |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,266,545 A | 5/1981 | Moss |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,375,217 A | 3/1983 | Arkans |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,722,332 A | 2/1988 | Saggers |
| 4,727,868 A | 3/1988 | Szycher et al. |
| 4,733,659 A | 3/1988 | Edenbaum et al. |
| 4,743,232 A | 5/1988 | Kruger |
| 4,758,220 A | 7/1988 | Sundblom et al. |
| 4,770,490 A | 9/1988 | Gruenewald et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,902,565 A | 2/1990 | Brook et al. |
| 4,906,233 A | 3/1990 | Moriuchi et al. |
| 4,906,240 A | 3/1990 | Reed et al. |
| 4,917,112 A | 4/1990 | Kalt |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,000,741 A | 3/1991 | Kalt |
| 5,018,515 A | 5/1991 | Gilman |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,106,629 A | 4/1992 | Cartmell et al. |
| 5,134,994 A | 8/1992 | Say |
| 5,149,331 A | 9/1992 | Ferdman et al. |
| 5,160,315 A | 11/1992 | Heinecke et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,380,294 A | 1/1995 | Persson |
| 5,423,737 A | 6/1995 | Cartmell et al. |
| 5,429,593 A | 7/1995 | Matory |
| 5,435,009 A | 7/1995 | Schild et al. |
| 5,437,622 A | 8/1995 | Carion |
| 5,437,651 A | 8/1995 | Todd et al. |
| 5,489,262 A | 2/1996 | Cartmell et al. |
| 5,497,788 A | 3/1996 | Inman et al. |
| 5,520,629 A | 5/1996 | Heinecke et al. |
| 5,527,293 A | 6/1996 | Zamierowski |
| 5,538,502 A | 7/1996 | Johnstone |
| 5,549,584 A | 8/1996 | Gross |
| 5,556,375 A | 9/1996 | Ewall |
| 5,607,388 A | 3/1997 | Ewall |
| 5,628,230 A | 5/1997 | Flam |
| 5,636,643 A | 6/1997 | Argenta et al. |
| 5,645,081 A | 7/1997 | Argenta et al. |
| 5,653,244 A | 8/1997 | Shaw |
| 5,792,088 A | 8/1998 | Felder et al. |
| 5,827,246 A * | 10/1998 | Bowen .................. 604/313 |
| 5,844,013 A | 12/1998 | Kenndoff et al. |
| 5,866,249 A | 2/1999 | Yarusso et al. |
| 5,950,238 A | 9/1999 | Klein |
| 6,071,267 A | 6/2000 | Zamierowski |
| 6,086,450 A | 7/2000 | Mankovitz |
| 6,109,267 A | 8/2000 | Shaw et al. |
| 6,135,116 A | 10/2000 | Vogel et al. |
| 6,162,960 A | 12/2000 | Klein |
| 6,213,840 B1 | 4/2001 | Han |
| 6,241,747 B1 | 6/2001 | Ruff |
| 6,270,910 B1 | 8/2001 | Jaeger et al. |
| 6,287,316 B1 | 9/2001 | Agarwal et al. |
| 6,345,623 B1 | 2/2002 | Heaton et al. |
| 6,361,397 B1 | 3/2002 | Mankovitz et al. |
| 6,420,622 B1 | 7/2002 | Johnston et al. |
| 6,440,093 B1 | 8/2002 | McEwen et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,648,862 B2 | 11/2003 | Watson |
| 6,685,681 B2 | 2/2004 | Lockwood et al. |
| 6,752,794 B2 * | 6/2004 | Lockwood et al. .......... 604/313 |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,867,342 B2 | 3/2005 | Johnston et al. |
| D503,509 S | 4/2005 | Bell et al. |
| 6,936,037 B2 | 8/2005 | Bubb et al. |
| 6,951,553 B2 | 10/2005 | Bubb et al. |
| 7,004,915 B2 | 2/2006 | Boynton et al. |
| 7,070,584 B2 | 7/2006 | Johnson et al. |
| 7,090,647 B2 | 8/2006 | Mimura et al. |
| 7,135,007 B2 | 11/2006 | Scott et al. |
| 7,144,294 B2 | 12/2006 | Bell et al. |
| 7,195,624 B2 | 3/2007 | Lockwood et al. |
| 7,201,063 B2 | 4/2007 | Taylor |
| 7,201,263 B2 | 4/2007 | Osada et al. |
| 7,214,202 B1 | 5/2007 | Vogel et al. |
| 7,316,672 B1 | 1/2008 | Hunt et al. |
| 7,361,184 B2 | 4/2008 | Joshi |
| 7,381,211 B2 * | 6/2008 | Zamierowski .................. 606/216 |
| 7,455,681 B2 | 11/2008 | Wilke et al. |
| 7,504,549 B2 | 3/2009 | Castellani et al. |
| 7,520,872 B2 | 4/2009 | Biggie et al. |

(56) References Cited

U.S. PATENT DOCUMENTS

| | | | |
|---|---|---|---|
| 7,532,953 B2 | 5/2009 | Vogel et al. | |
| 7,569,742 B2 | 8/2009 | Haggstrom et al. | |
| 7,699,831 B2 | 4/2010 | Bengtson et al. | |
| 7,700,819 B2 * | 4/2010 | Ambrosio et al. | 604/290 |
| 8,029,498 B2 * | 10/2011 | Johnson et al. | 604/543 |
| 8,100,848 B2 | 1/2012 | Wilkes et al. | |
| 2001/0029956 A1 | 10/2001 | Argenta et al. | |
| 2001/0043943 A1 | 11/2001 | Coffey | |
| 2002/0077661 A1 | 6/2002 | Saadat | |
| 2002/0115951 A1 | 8/2002 | Norstrem et al. | |
| 2002/0120185 A1 | 8/2002 | Johnson et al. | |
| 2002/0143286 A1 | 10/2002 | Tumey | |
| 2003/0040691 A1 | 2/2003 | Griesbach et al. | |
| 2003/0109816 A1 | 6/2003 | Lachenbruch et al. | |
| 2003/0212359 A1 | 11/2003 | Butler | |
| 2004/0039415 A1 | 2/2004 | Zamierowski | |
| 2004/0064111 A1 | 4/2004 | Lockwood et al. | |
| 2004/0064132 A1 | 4/2004 | Boehringer et al. | |
| 2004/0242119 A1 | 12/2004 | Francis | |
| 2004/0243073 A1 | 12/2004 | Lockwood et al. | |
| 2005/0209574 A1 | 9/2005 | Boehringer et al. | |
| 2005/0222544 A1 | 10/2005 | Weston | |
| 2005/0228329 A1 | 10/2005 | Boehringer et al. | |
| 2006/0041247 A1 | 2/2006 | Petrosenko et al. | |
| 2006/0064049 A1 | 3/2006 | Marcsen | |
| 2006/0079852 A1 | 4/2006 | Bubb et al. | |
| 2006/0149171 A1 | 7/2006 | Vogel et al. | |
| 2006/0173253 A1 | 8/2006 | Ganapathy | |
| 2006/0189910 A1 | 8/2006 | Johnson et al. | |
| 2006/0213527 A1 | 9/2006 | Argenta et al. | |
| 2006/0264796 A1 | 11/2006 | Flick et al. | |
| 2007/0021697 A1 | 1/2007 | Ginther et al. | |
| 2007/0027414 A1 | 2/2007 | Hoffman et al. | |
| 2007/0066946 A1 | 3/2007 | Haggstrom et al. | |
| 2007/0078366 A1 | 4/2007 | Haggstrom et al. | |
| 2007/0135777 A1 | 6/2007 | Greene et al. | |
| 2007/0185426 A1 | 8/2007 | Ambrosio | |
| 2007/0219497 A1 | 9/2007 | Johnson | |
| 2007/0219513 A1 | 9/2007 | Lina et al. | |
| 2007/0219532 A1 | 9/2007 | Karpowicz et al. | |
| 2008/0004549 A1 | 1/2008 | Anderson et al. | |
| 2008/0009812 A1 | 1/2008 | Riesinger | |
| 2008/0039763 A1 | 2/2008 | Sigurjonsson et al. | |
| 2008/0076844 A1 | 3/2008 | Van Sumeren et al. | |
| 2008/0103462 A1 | 5/2008 | Wenzel | |
| 2008/0119802 A1 | 5/2008 | Riesinger | |
| 2009/0043268 A1 | 2/2009 | Eddy et al. | |
| 2009/0177051 A1 | 7/2009 | Arons et al. | |
| 2009/0204084 A1 | 8/2009 | Blott et al. | |
| 2009/0204085 A1 | 8/2009 | Biggie et al. | |
| 2009/0227968 A1 | 9/2009 | Vess | |
| 2009/0234307 A1 | 9/2009 | Vitaris | |
| 2009/0264807 A1 | 10/2009 | Haggstrom | |
| 2009/0293887 A1 | 12/2009 | Wilkes et al. | |
| 2010/0179515 A1 * | 7/2010 | Swain et al. | 604/543 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 39 07 522 C1 | 4/1990 |
| DE | 43 06 478 A1 | 9/1994 |
| DE | 295 04 378 U1 | 10/1995 |
| DE | 20 2006 007877 | 7/2006 |
| DE | 10 2005 007016 A1 | 8/2006 |
| EP | 0100148 A1 | 2/1984 |
| EP | 0117632 A2 | 9/1984 |
| EP | 0161865 A2 | 11/1985 |
| EP | 0330373 A2 | 8/1989 |
| EP | 0358302 A2 | 3/1990 |
| EP | 0424165 A1 | 4/1991 |
| EP | 0691113 A1 | 1/1996 |
| EP | 1018967 B1 | 8/2004 |
| FR | 1163907 A | 10/1958 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 95/14451 A1 | 6/1995 |
| WO | WO 96/05873 | 2/1996 |
| WO | WO 97/18007 | 5/1997 |
| WO | WO 99/13793 | 3/1999 |
| WO | WO 00/07653 A1 | 2/2000 |
| WO | WO 03/057071 A2 | 7/2003 |
| WO | WO 03/057307 A1 | 7/2003 |
| WO | WO 03/086262 A2 | 10/2003 |
| WO | WO 2005123170 A1 | 12/2005 |
| WO | WO 2006/012745 A1 | 2/2006 |
| WO | WO 2007/031762 | 3/2007 |
| WO | WO 2007/033679 | 3/2007 |
| WO | WO 2007/041642 A2 | 4/2007 |
| WO | WO 2008/054312 A1 | 5/2008 |
| WO | WO 2008/063281 A2 | 5/2008 |
| WO | WO 2009/019496 A2 | 2/2009 |
| WO | WO 2009/047524 A2 | 4/2009 |
| WO | WO 2009/071926 A1 | 6/2009 |

OTHER PUBLICATIONS

Response filed Oct. 20, 2011 for U.S. Appl. No. 12/475,285.
Interview Summary date mailed Oct. 26, 2011 for U.S. Appl. No. 12/475,285.
Response filed Sep. 13, 2011 for U.S. Appl. No. 12/475,380.
Non-Final Office Action date mailed Sep. 15, 2011 for U.S. Appl. No. 12/475,398.
Response filed Oct. 5, 2011 for U.S. Appl. No. 12/475,301.
Response filed Oct. 18, 2011 for U.S. Appl. No. 12/475,367.
Response filed Oct. 20, 2011 for U.S. Appl. No. 12/475,319.
Interview Summary date mailed Oct. 26, 2011 for U.S. Appl. No. 12/475,319.
Restriction Requirement date mailed Oct. 12, 2011 for U.S. Appl. No. 12/475,328.
Response filed Oct. 19, 2011 for U.S. Appl. No. 12/475,328.
Notice of Allowance date mailed Sep. 16, 2011 for U.S. Appl. No. 12/475,257.
Response filed Oct. 20, 2011 for U.S. Appl. No. 12/475,407.
Interview Summary date mailed Oct. 27, 2011 for U.S. Appl. No. 12/475,407.
Response filed Oct. 25, 2011 for U.S. Appl. No. 12/475,373.
Interview Summary date mailed Oct. 27, 2011 for U.S. Appl. No. 12/475,373.
Non-Final Rejection mailed Jul. 20, 2011 for U.S. Appl. No. 12/475,301.
Restriction Requirement mailed Aug. 16. 2011 for U.S. Appl. No. 12/475,380.
Restriction Requirement mailed May 10, 2011 for U.S. Appl. No. 12/475,285.
Response to Restriction Requirement filed Jun. 7, 2011 for U.S. Appl. No. 12/475,285.
Non-Final Rejection mailed Aug. 19, 2011 for U.S. Appl. No. 12/475,285.
Restriction Requirement mailed May 10, 2011 for U.S. Appl. No. 12/475,367.
Response to Restriction Requirement filed Jun. 7, 2011 for U.S. Appl. No. 12/475,367.
Non-Final Rejection mailed Aug. 23, 2011 for U.S. Appl. No. 12/475,367.
Restriction Requirement mailed May 17, 2011 for U.S. Appl. No. 12/475,319.

(56) References Cited

OTHER PUBLICATIONS

Response to Restriction Requirement filed Jun. 7, 2011 for U.S. Appl. No. 12/475,319.
Non-Final Rejection mailed Aug. 18, 2011 for U.S. Appl. No. 12/475,319.
Non-Final Rejection mailed May 24, 2011 for U.S. Appl. No. 12/475,257.
Response to Non-Final Rejection filed Jul. 27, 2011 for U.S. Appl. No. 12/475,257.
Restriction Requirement mailed May 9, 2011 for U.S. Appl. No. 12/475,388.
Response to Restriction Requirement filed Jun. 7, 2011 for U.S. Appl. No. 12/475,388.
Non-Final Rejection mailed Sep. 7, 2011 for U.S. Appl. No. 12/475,388.
Restriction Requirement mailed Apr. 29, 2011 for U.S. Appl. No. 12/475,231.
Response to Restriction Requirement filed May 19, 2011 for U.S. Appl. No. 12/475,231.
Non-Final Rejection mailed Sep. 6, 2011 for U.S. Appl. No. 12/475,231.
Restriction Requirement mailed May 12, 2011 for U.S. Appl. No. 12/475,407.
Response to Restriction Requirement filed Jun. 7, 2011 for U.S. Appl. No, 12/475,407.
Non-Final Rejection mailed Aug. 23, 2011 for U.S. Appl. No. 12/475,407.
Restriction Requirement mailed May 9, 2011 for U.S. Appl. No. 12/475,373.
Response to Restriction Requirement filed Jun. 7, 2011 for U.S. Appl. No. 12/475,373.
Non-Final Rejection mailed Aug. 23, 2011 for U.S. Appl. No. 12/475,373.
International Search Report for PCT International Application No. PCT/2009/045743 date mailed Aug. 20, 2009.
Notice of Allowance mailed Sep. 16, 2011 for U.S. Appl. No. 12/475,257.
Richard S. Laskin, et al "Minimally Invasive Total Knee Replacement Through a Mini-Midvast Incision: An Outcome Study" Surgical Technology International XIII, 2004; 231-8.
A. Dee, "The successful management of a dehisced surgical wound with TNP following femoropopliteal bypass". Journal of Wound Care, vol. 16, No. 1, Jan. 2007.
Ogazon, e of Vacuum-Assisted Closure in the Treatment of Surgical Infection Sites Cir. Mar.-Apr. 2006; 74(2): 107-13 Spanish.
Timmenga, "The Effects of Mechanical Stress on Healing Skin Wounds: An Experimental Study in Rabbits ing Tissues Expansions," British Journal of Plastic Surgery 1991; 44(7): 514-519.
Cunningham, "Development of in-vitro model to simulate Dermal Wound Bed Interaction with GranuFoam and Gauze Dressing under Sub Atmospheric Pressure," RPT 111-05-02, device implant innovations 2006.
Delalleau, "Characterization of the Mechanical Properties of Skin by Inverse Analysis Combined with the Indentation Test" Journal of Biomechanics 39 (2006) 1603-1610.
Pailler-Mattei, "Study of Adhesion Forces and Mechanical Properties of Human Skin in vivo" J. Adhesion Sci. Technol., vol. 18, No. 15-16, pp. 1739-1758 (2004).
Khatyr, "Model of the Viscoelastic Behaviour of Skin in vivo and Study of Anisotropy," Skin Research and Technology 2004; 10:96-103.
Wilkes, "3D Strain Measurement in Soft Tissue: Demonstration of a Novel Inverse Finite Element Model Algorithm on MicroCT Images of a Tissue Phantom Exposed to Negative Pressure Wound Therapy," Journal of the Mechanical Behaviour of Biomedical Materials (2008), pp. 1-16.
Diridollou, "In vivo Model of the Mechanical Properties of the Human Skin under Suction", Skin Research and Technology, 2000; 6:214-221.
Woo, "Structural Model to Describe the Non-Linear Stress-Strain Behavior for Parallel-Fibered Collageno Tissues," Journal of Biomechanical Engineering, Nov. 1989, vol. 111/361.
International Search Report and Written Opinion date mailed Oct. 20, 2009; PCT International Application No. PCT/2009/045747.
International Search Report and Written Opinion date mailed Oct. 16, 2009; PCT International Application No. PCT/2009/045752.
Partial International Search Report and Written Opinion date mailed Oct. 7, 2009; PCT International Application No. PCT/2009/045755.
Internatioanl Search Report and Written Opinion date mailed Mar. 12, 2010; PCT International Application No. PCT/2009/045755.
International Search Report and Written Opinion date mailed Oct. 26, 2009; PCT International Application No. PCT/2009/045751.
International Search Report and Written Opinion date mailed Oct. 14, 2009; PCT International Application No. PCT/2009/045746.
International Search Report and Written Opinion date mailed Oct. 27, 2009; PCT International Application No. PCT/2009/045744.
Partial International Search Report and Written Opinion date mailed Oct. 19, 2009; PCT Internatioanl Application No. PCT/2009/045742.
Partial International Search Report and Written Opinion date mailed Nov. 2, 2009; PCT International Application No. PCT/2009/045750.
International Search Report and Written Opinion date mailed Oct. 21, 2009; PCT International Application No. PCT/2009/045749.
International Search Report and Written Opinion date mailed Nov. 11, 2009; PCT International Application No. PCT/2009/045754.
International Search Report and Written Opinion date mailed Dec. 11, 2009; PCT International Application No. PCT/2009/045753.
International Search Report and Written Opinion date mailed Feb. 25, 2010; PCT International Application No. PCT/2009/045750.
Non-Final Office Action date mailed Dec. 28, 2011 for U.S. Appl. No. 12/475,285.
Non-Final Office Action date mailed Nov. 8, 2011 for U.S. Appl. No. 12/475,380.
Response filed Nov. 22, 2011 for U.S. Appl. No. 12/475,398.
Interview Summary date mailed Nov. 29, 2011 for U.S. Appl. No. 12/475,398.
Notice of Allowance date mailed Nov. 14, 2011 for U.S. Appl. No. 12/475,301.
Notice of Allowance date mailed Jan. 3, 2012 for U.S. Appl. No. 12/475,319.
Non-Final Office Action date mailed Dec. 9, 2011 for U.S. Appl. No. 12/475,328.
Response filed Nov. 11, 2011 for U.S. Appl. No. 12/475,388.
Interview Summary date mailed Dec. 5, 2011 for U.S. Appl. No. 12/475,388.
Response filed Nov. 11, 2011 for U.S. Appl. No. 12/475,231.
Interview Summary date mailed Dec. 5, 2011 for U.S. Appl. No. 12/475,231.
Notice of Allowance date mailed Jan. 9, 2012 for U.S. Appl. No. 12/475,407.
Response filed Jan. 19, 2012 for U.S. Appl. No. 12/475,380.
Interview Summary date mailed Jan. 25, 2012 for U.S. Appl. No. 12/475,380.
Notice of Allowance date mailed Feb. 15, 2012 for U.S. Appl. No. 12/475,380.
Response filed Feb. 9, 2012 for U.S. Appl. No. 12/475,328.
Notice of Allowance date mailed Feb. 17, 2012 for U.S. Appl. No. 12/475,388.
Notice of Allowance date mailed Jan. 20, 2012 for U.S. Appl. No. 12/475,231.
Notice of Allowance date mailed Jan. 10, 2012 for U.S. Appl. No. 12/475,373.
N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., JR., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor: Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.
G. Živadinović, V. Ð ukić, Ž. Maksimović, Ð . Radak, and P. Peška, "Vacuum Therapy in the Treatment of Peripheral Blood Vessels," *Timok Medical Journal* 11 (1986), pp. 161-164 (certified translation).
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

SYSTEM AND METHOD FOR SEALING AN INCISIONAL WOUND

CROSS-REFERENCE TO RELATED APPLICATIONS

This application claims the benefit of U.S. Provisional Application No. 61/329,764, filed Apr. 30, 2010, which is hereby incorporated by reference.

BACKGROUND OF THE INVENTION

1. Field of the Invention

The present disclosure relates generally to medical treatment systems and in particular to apparatuses and systems suitable for use as scaffolds in the treatment of wounds.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formation of granulation tissue. Typically, reduced pressure has been applied to tissue through a porous pad or other manifolding device. The porous pad contains pores that are capable of distributing reduced pressure to the tissue and channeling fluids that are drawn from the tissue. The porous pad often is incorporated into a dressing having other components that facilitate treatment. A scaffold can also be placed into a defect to support tissue growth into the defect. The scaffold is usually bioabsorbable, leaving new tissue in its place.

Synthetic and biologic scaffolds have been utilized to provide three-dimensional frameworks for augmenting endogenous cell attachment, migration, and colonization. To date, nearly all scaffolds have been designed with the idea that they can be made to work with the biology. Traditional scaffolding technologies, however, rely on the passive influx of endogenous proteins, cytokines, growth factors, and cells into the interstitium of the porous scaffold. As such, the colonization of endogenous cells into the scaffold is limited by the distance away from vascular elements, which provide nutrient support within a diffusion limit of the scaffold, regardless of tissue type. In addition, the scaffolds can also elicit an immunogenic or foreign body response that leads to an elongated repair process. Taken together, these complications can all lead to less than desired functional tissue regeneration at the injury site.

It would therefore be advantageous to provide additional systems and apparatuses for the repair or regeneration of tissues resulting from specific injuries or incisions at various tissue sites. The present invention provides such systems and apparatuses.

SUMMARY

The systems, apparatuses, and methods of the illustrative embodiments described herein include an apparatus for treating an incisional wound having incisional walls. The apparatus includes a conduit having a first end for receiving reduced pressure and a second end. The apparatus further includes a scaffold. The scaffold has opposing surfaces for positioning adjacent the incisional walls and is fluidly coupled to the second end of the conduit for receiving the reduced pressure. The scaffold is generally elongated in shape and has a thickness between the opposing surfaces that is sufficiently thin for positioning within the incisional wound. The apparatus further includes an internal manifold that has a primary flow channel extending generally longitudinally within the scaffold and between the opposing surfaces of the scaffold. The internal manifold is fluidly coupled to the second end of the conduit. The application of the reduced pressure through the scaffold and the internal manifold induces tissue apposition between the incisional walls.

According to another illustrative embodiment, a system for treating an incisional wound having incisional walls includes a pressure source to supply reduced pressure, a conduit fluidly coupled to the pressure source that has a first end for receiving the reduced pressure and a second end, and a scaffold fluidly coupled to the second end of the conduit. The scaffold has opposing surfaces, is formed from a porous material, and is generally elongated in shape. The system further includes an internal manifold that has a primary flow channel extending generally longitudinally within the scaffold between the opposing surfaces. The internal manifold is fluidly coupled to the second end of the conduit. The application of the reduced pressure through the scaffold and the internal manifold induces tissue apposition between the incisional walls.

According to another illustrative embodiment, a system for treating an incisional wound having incisional walls includes a pressure source to supply reduced pressure, a conduit fluidly coupled to the pressure source that has a first end for receiving the reduced pressure and a second end, and a scaffold fluidly coupled to the second end of the conduit. The scaffold has opposing surfaces, is formed from a porous material, and is generally elongated in shape. The system further includes an internal manifold that has a primary flow channel extending generally longitudinally within the scaffold between the opposing surfaces. The internal manifold is fluidly coupled to the second end of the conduit. The internal manifold further includes tributary flow channels fluidly coupled to the primary flow channel and extending generally transversely within the scaffold between the opposing surfaces. The tributary flow channels extend generally perpendicular from the primary flow channel. The application of the reduced pressure through the scaffold and the internal manifold induces tissue apposition between the incisional walls.

According to yet another illustrative embodiment, a method for treating an incisional wound having incisional walls includes fluidly coupling a conduit to a source of reduced pressure, wherein the conduit has a first end for receiving reduced pressure and a second end. The scaffold is fluidly coupled to the second end of the conduit for receiving the reduced pressure, wherein the scaffold is formed from sufficiently thin porous material having an internal manifold extending generally longitudinally between opposing surfaces of the scaffold. The opposing surfaces of the scaffold are positioned between the incisional walls of the incisional wound and the internal manifold is fluidly coupled to the second end of the conduit. The incisional wound is surgically closed and reduced pressure is provided through the conduit to the scaffold and the internal manifold onto the incisional wound, whereby the scaffold induces tissue apposition between the incisional walls.

Other objects, features, and advantages of the illustrative embodiments will become apparent with reference to the drawings and detailed description that follows.

DETAILED DESCRIPTION

In the following detailed description of the illustrative embodiments, reference is made to the accompanying drawings that form a part herein. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
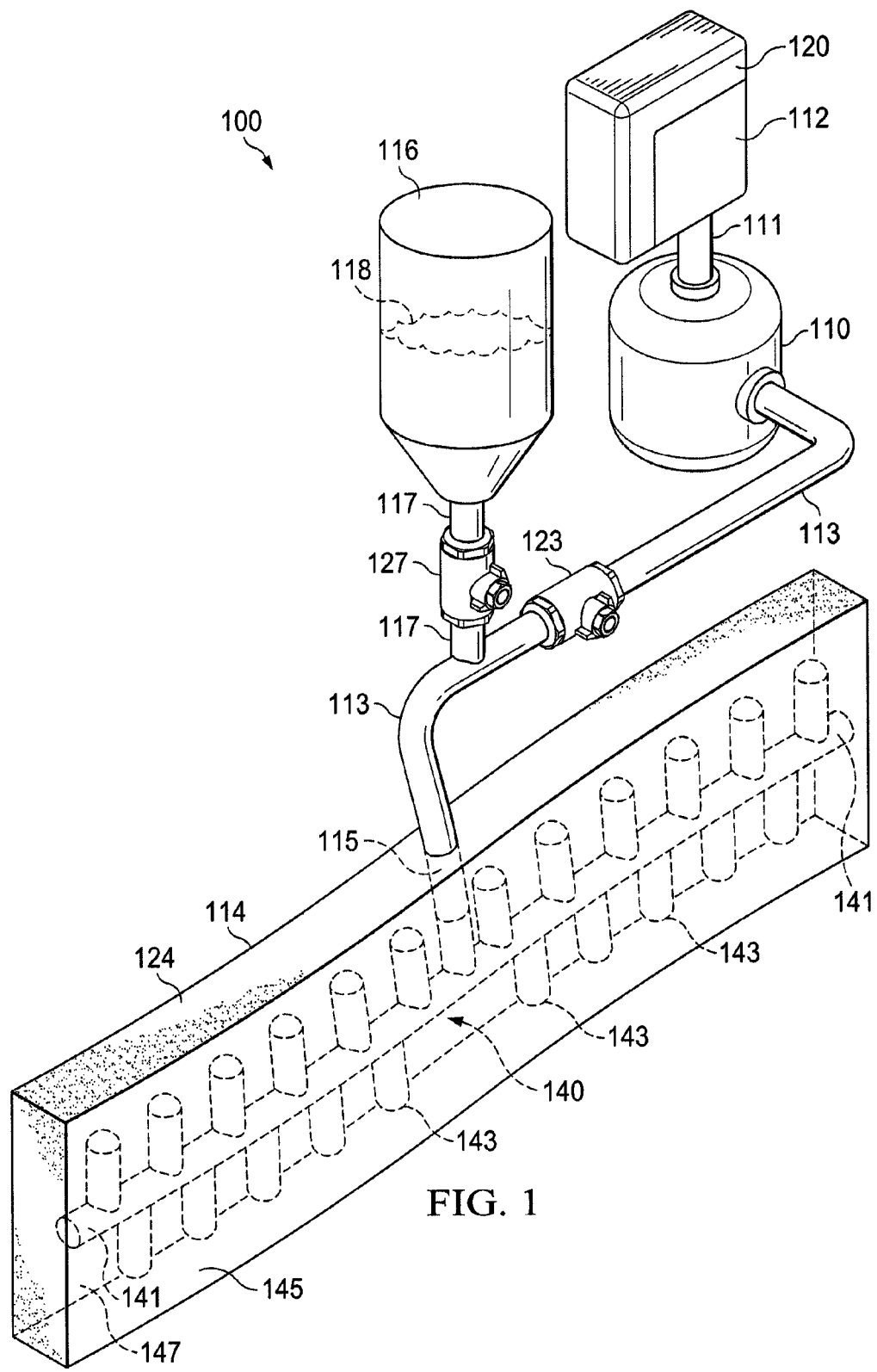
FIG. 1 is a schematic, perspective view of a reduced pressure treatment system including a scaffold according to one illustrative embodiment.
Figure 2:
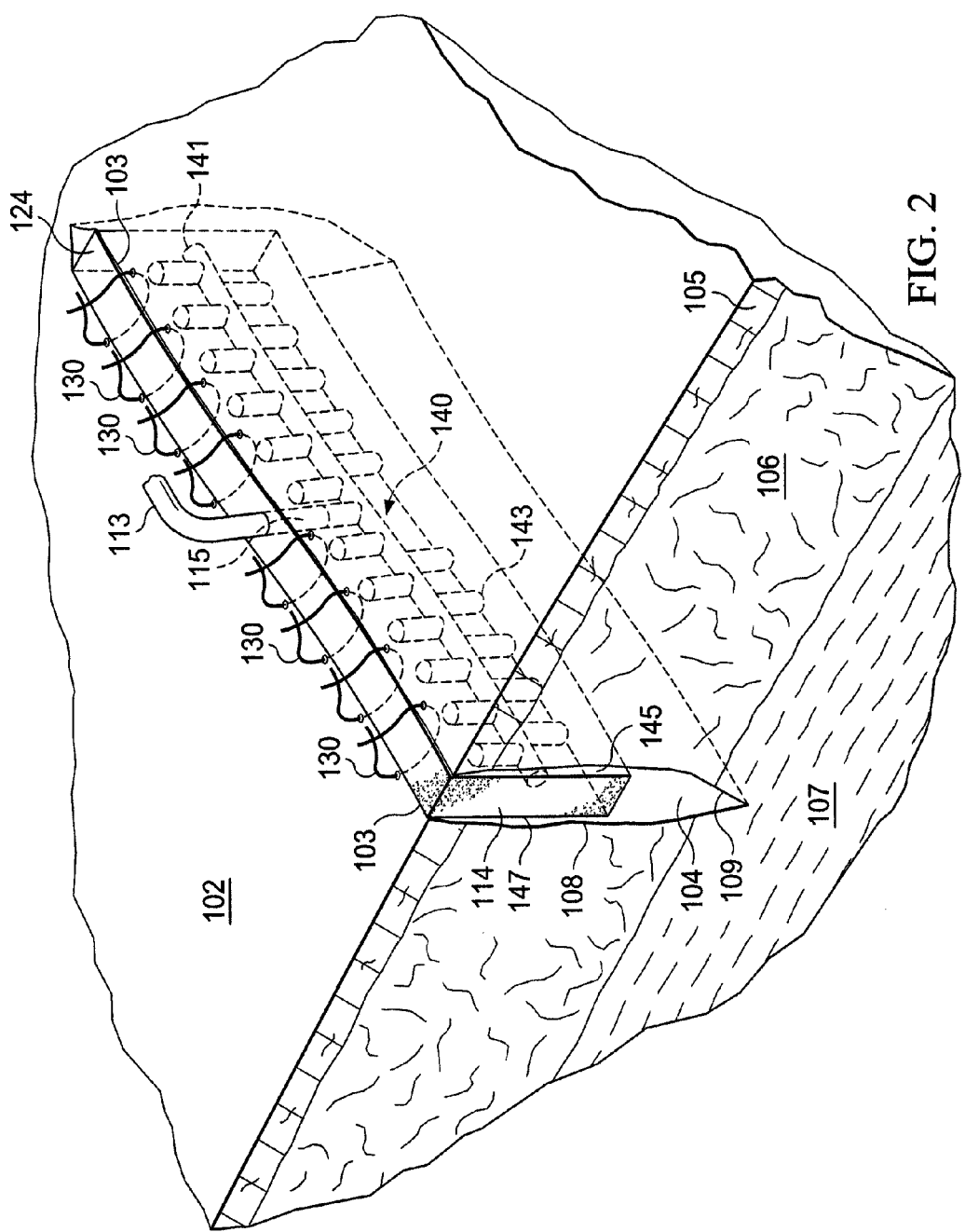
FIG. 2 is a schematic, cross-sectional, perspective view of an incisional wound and the scaffold shown in FIG. 1 positioned within the incisional wound.

Referring to FIGS. 1 and 2, a reduced pressure treatment system 100 for applying a reduced pressure to a tissue site 102 of a patient according to an illustrative embodiment is shown. The reduced pressure treatment system 100 applies reduced pressure to an incisional wound 104 through an incisional opening 103 in epidermis 105 extending through dermis 106 into the fascial layers or subcutaneous tissues 107 at the tissue site 102. The term "incisional wound" refers to severed tissue at a tissue site such as, for example, a laceration, incision, or puncture that may have been caused by trauma, surgery, or degeneration. For example, an incisional wound may be an incision or puncture made by a surgeon in otherwise healthy tissue that extends up to 40 cm or more in length. In this sense, the incisional wound 104 is substantially a long and narrow shape, elongated shape, wherein the length represents the longitudinal axis of the incisional wound 104. Incisional wounds may extend to different depths extending up to 15 cm or more, or be subcutaneous depending on the type of tissue and the cause of the incision. The depth represents the transverse axis of the incisional wound 104. The incisional wound 104 is surrounded by tissue adjacent the incisional opening 103 at the tissue site 102 and is formed by incisional walls 108 and 109. Although the incisional wound 104 is shown as an epidermal incision at the tissue site 102, the incisional wound 104 may also be, for example, an incision in an organ adjacent a fistula. Subcutaneous, absorbable sutures (not shown) may be placed in one or more fascial layers or the subcutaneous tissues 107.

The system 100 comprises a canister 110 having a filter (not shown) contained with the canister 110 and a reduced pressure source 112 coupled in fluid communication with the canister 110 via a first conduit 111. The system 100 further comprises a scaffold 114 positioned within the incisional wound 104 between the incisional walls 108, 109. The scaffold 114 includes an upper edge portion 124 positioned adjacent the incisional opening 103 of the incisional wound 104, a lower edge portion 125, and opposing, interfacial surfaces 145 and 147 positioned adjacent the faces of the incisional walls 109 and 108, respectively, of the incisional wound 104. The scaffold 114 is coupled in fluid communication with the reduced pressure source 112 through the canister 110 via a second conduit 113 which is fluidly coupled to the scaffold 114 by a conduit connector 115. The system 100 may also comprise a fluid supply 116 coupled in fluid communication to the scaffold 114 via a third conduit 117 either directly (not shown) or indirectly through the second conduit 113 for delivering a fluid 118 to the incisional wound 104 at the tissue site 102.

The reduced pressure source 112 is an electrically-driven vacuum pump. In another implementation, the reduced pressure source 112 instead may be a manually-actuated or manually-charged pump that does not require electrical power. The reduced pressure source 112 may be any other type of reduced pressure pump, or alternatively a wall suction port such as those available in hospitals and other medical facilities. The reduced pressure source 112 may be housed within or used in conjunction with a reduced pressure treatment unit 120 which may also contain a processing unit, sensors, alarm indicators, memory, databases, software, display units, and user interfaces that further facilitate the application of reduced pressure treatment to the tissue site 102. In one example, a sensor or switch (not shown) may be disposed at or near the reduced pressure source 112 to determine a source pressure generated by the reduced pressure source 112. The sensor may communicate with a processing unit (not shown) that monitors and controls the reduced pressure that is delivered by the reduced pressure source 112. The canister 110 may be a fluid reservoir, or collection member, to filter or hold exudates and other fluids removed from the tissue site 102. In one embodiment, the canister 110 and the reduced pressure source 112 are integrated into a single housing structure.

The fluid supply 116 may be used to deliver growth and/or healing agents to the scaffold 114 for the incisional wound 104 including, without limitation, an antibacterial agent, an antiviral agent, a cell-growth promotion agent, an irrigation fluid, or other chemically active agents. The system 100 further comprises a first valve 127 positioned in the third conduit 117 to control the flow of fluid 118 to the scaffold 114, and a second valve 123 positioned in the second conduit 113 between the reduced pressure source 112 and the juncture between the second conduit 113 and the third conduit 117 to control the flow of reduced pressure. The processing unit of the reduced pressure treatment unit 120 is operatively connected to the first and second valves 127, 123 to control the delivery of reduced pressure and/or fluid from the fluid supply 116, respectively, to the scaffold 114 as required by the particular therapy being administered to the patient. The fluid supply 116 may deliver the fluids as indicated above, but may also deliver air to the scaffold 114 to promote healing and facilitate drainage of the incisional wound 104. The fluid 118 may be gas or liquid, and may contain growth factors, healing factors, or other substances to treat the incisional wound 104 at the tissue site 102. For example, the fluid 118 may be water, saline, or dye saline.

The term "scaffold" as used herein refers to a substance or structure applied to or positioned in a wound or defect that provides a structural matrix for the growth of cells and/or the formation of tissue. A scaffold is a three-dimensional, porous structure having dimensions roughly corresponding to the shape of the specific wound defect. The scaffold 114 may be infused with, coated with, or comprised of cells, growth factors, extracellular matrix components, nutrients, proteins, or other substances to promote cell growth. The scaffold 114 may possess characteristics of a manifold by directing the flow of fluids through its structural matrix. For example, the scaffold 114 may take on the characteristics of a manifold by directing reduced pressure or delivering fluids to a tissue site, or removing fluids from a tissue site. As used herein, the term "manifold" refers to a substance or structure that is provided to assist in directing reduced pressure or delivering fluids to a tissue site, or removing fluids from a tissue site. A manifold can include a plurality of flow channels or pathways that are interconnected to improve distribution of fluids provided to and removed from the area of tissue around the manifold. Examples of manifolds may include, without limitation, devices that have structural elements arranged to form flow channels, cellular foams such as open-cell foam, porous tissue collections, and liquids, gels and foams that include or cure to include flow channels. The scaffold 114 possesses the characteristics of a manifold as described above.

The scaffold 114 may be a biologic or synthetic scaffold used to support protein adhesion and cellular in-growth for tissue repair and regeneration. The current state of the art in scaffold technology relies upon the inherent characteristics of the surrounding tissue space for the adsorption of proteins and migration of cells. The scaffold 114 for use according to the invention, and coupled with its function as a manifold, provides physical guidance to direct the pathway of fluid flow within the incisional wound 104, creating avenues for the movement and migration of adhesive proteins and cells, respectively, which are integral to the establishment of a provisional matrix in predetermined patterns of organization within the tissue space. The methods and apparatuses described for fluid flow-induced generation of tissues have direct implications into the design of the scaffold 114. In certain aspects, the scaffold 114 may be a reticulated structure, such as, for example, a reticulated foam, comprising a high void fraction for improved bioabsorption properties.

Non-limiting examples of suitable scaffold materials include extracellular matrix proteins such as fibrin, collagen or fibronectin, and synthetic or naturally occurring polymers, including bioabsorbable or non-bioabsorbable polymers, such as polylactic acid (PLA), polyglycolic acid (PGA), poly-lactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyethylene glycols, poloxamers, polyphosphazenes, polyanhydrides, polyamino acids, polyortho esters, polyacetals, polycyanoacrylates, polyurethanes, polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon. The scaffold 114 can also comprise ceramics such as hydroxyapatite, corallin apatite, calcium phosphate, calcium sulfate, calcium carbonate or other carbonates, bioglass, allografts, autografts, xenografts, decellularized tissues, or composites of any of the above. In particular embodiments, the scaffold 114 comprises collagen, polylactic acid (PLA), polyglycolic acid (PGA), polylactide-co-glycolide (PLGA), a polyurethane, a polysaccharide, an hydroxyapatite, or a polytherylene glycol. Additionally, the scaffold 114 may comprise combinations of any two, three or more materials, either in separate areas of the scaffold 114, or combined noncovalently, or covalently (e.g., copolymers such as a polyethylene oxide-polypropylene glycol block copolymers, or terpolymers), or combinations thereof.

In one embodiment, the scaffold 114 is formed from a scaffold material comprising PLGA fibers formed by a felting process that also functions as a manifold as described above. Such material known as Scaftex™ is available from Biomedical Structures, Inc. Any of the biodegradable or bioresorbable materials listed above that are reticulated and possess a high void fraction (low mass for degradation or resorption) may be used. The elastomeric materials, pliable materials, and gels are embodiments that are preferred for soft-tissue applications such as the incisional wound 104. The scaffold 114 is relatively thin between the opposing, interfacial surfaces 145, 147 which are positioned adjacent the incisional walls 109, 108, respectively, of the incisional wound 104. In one non-limiting example, the scaffold 114 may be approximately 0.25 mm to 3.0 mm thick between the opposing, interfacial surfaces 145, 147. Comparing the thickness of the scaffold 114 to the length and depth of the incisional wound 104, the scaffold 114 may be described as being relatively thin. In one embodiment, a ratio of the length to the thickness of the scaffold 114 is greater than about 10. Preferably, the scaffold 114 should be as thin as possible to fit within the incisional wound 104, minimizing the distance between the incisional walls 108, 109 to facilitate tissue apposition. Although the scaffold 114 is sufficiently thin, the material forming the scaffold 114 still comprises a matrix of pathways (not shown) to facilitate the flow of fluid between the incisional walls 108, 109. These pathways of the scaffold 114 extend through the scaffold 114 between the opposing, interfacial surfaces 145, 147 to induce tissue apposition by promoting the growth of tissue between the incisional walls 108, 109 as an interfacial scaffold matrix within the incisional wound 104.

The scaffold 114 may be of any size or shape depending on a variety of factors such as, for example, the type and size of the incisional wound 104 and the type of treatment being implemented to repair the wound. For example, the scaffold 114 may be substantially rectangular extending the full length of the incisional wound 104 along the longitudinal axis and the full depth of the incisional walls 108, 109 along the transverse axis. The scaffold 114 of such dimensions forms a full interfacial scaffold matrix between the two incisional walls 108, 109 to induce tissue apposition between the two. However, depending on the treatment, the scaffold 114 may only partially contact the incisional walls 108, 109. For example, the scaffold 114 may not extend to the bottom of the incisional wound 104 into the subcutaneous tissues 107. The upper edge portion 124 of the scaffold 114 may be positioned flush with the incisional opening 103 of the incisional wound 104 adjacent the epidermis 105, and secured within the incisional wound 104 by a plurality of sutures 130 that close the incisional wound 104 when stitched.

The scaffold 114 may further comprise an internal manifold structure 140 to supplement the flow of fluid through the reticulated pathways that already exist within the scaffold 114. The internal manifold structure 140 may comprise one or a plurality of primary flow channels 141 fluidly coupled to the conduit connector 115 that extend generally longitudinally through the scaffold 114 between the incisional walls 108, 109. The internal manifold structure 140 may also comprise additional tributary channels 143 fluidly coupled to one or more of the primary flow channels 141. The tributary channels 143 extend generally transversely within the scaffold 114 between the opposing, interfacial surfaces 145, 147 to further facilitate fluid flow over a larger area of the interfacial scaffold matrix within the incisional wound 104. The tributary channels 143 may extend from the primary flow channel 141 in any direction relative to the primary flow channel 141 and may form any shape to enhance the area of the scaffold 114 covering the interfacial surfaces 145, 147. For example, as shown in a specific, non-limiting embodiment, the tributary channels 143 extend in a direction generally perpendicular from the primary flow channel 141 in a linear direction as opposed to having a curved shape. Thus, the internal manifold structure 140 provides a supplemental matrix for fluid flow coextensive with the reticulated pathways of the scaffold 114 by using the plurality of primary flow channels 141 or a single primary channel that may include the plurality of tributary channels 143 or a combination of both. This supplemental matrix of the internal manifold structure 140 may be formed with a pattern that further induces apposition of the incisional walls 108, 109.

Although the primary flow channel 141 is shown as a generally tubular shape in the figures, the primary flow channel 141 may be a variety of different shapes as long as such flow channel extends generally longitudinally through the scaffold 114 between the incisional walls 108, 109. The primary flow channel 141 does not need to be straight, but may undulate longitudinally within the scaffold 114 between the upper edge portion 124 and lower edge portion 125. The primary flow channel 141 may also be an anisotropic material property of the scaffold 114 itself extending generally longitudinally between the incisional walls 108, 109. For example, the anisotropic property may be a differential resistance to fluid flow through interconnected pores within the scaffold 114 extending along a generally longitudinal axis of the scaffold 114. The anisotropic property may also be the alignment of pores and their interconnectivity within the scaffold 114, or the variation of pore size within the scaffold 114 that permits or facilitates fluid flow along a longitudinal axis of the scaffold 114. In another embodiment, the primary flow channel 141 may be formed by a bioresorbable tubing.

The tributary channels 143 may be asymmetric in shape and formed from anisotropic properties of the scaffold 114. In another embodiment, the tributary channels 143 may be formed by a bioresorbable tubing. Although inlets of the tributary channels 143 are shown extending from the surface of the primary flow channel 141, the tributary channels 143 may also extend from loci within the primary flow channel 141 and diverge within the scaffold 114 as non-parallel, asymmetric passages. The inlets of such tributary channels 143 are in fluid communication with the primary flow channel 141 to facilitate the flow of fluids between the incisional walls 108, 109. The inlets of several tributary channels 143 may also originate and diverge from a single locus within the primary flow channel 141 in a star-pattern, for example, generally in parallel with and between the incisional walls 108, 109.

Figure 3:
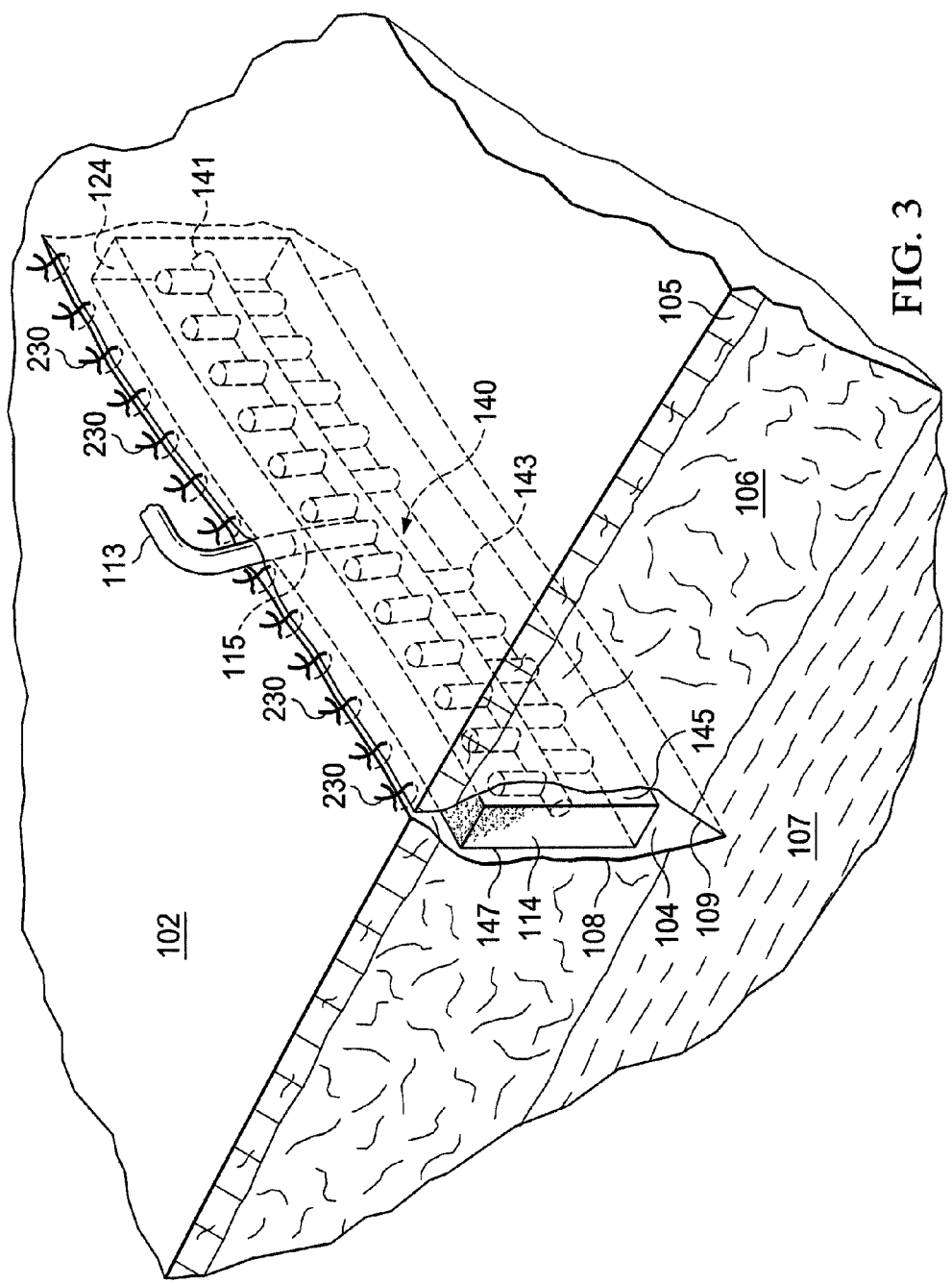
FIG. 3 is a schematic, cross-sectional, perspective view of an incisional wound and the scaffold shown in FIG. 1 positioned below the opening of the incisional wound.

Referring to FIG. 3, the scaffold 114 may be positioned within the incisional wound 104 so that the upper edge portion 124 of the scaffold 114 is seated below the epidermis 105 such that sutures 230 may be used to close the entire scaffold 114 within the incisional wound 104. Seating the upper edge portion 124 of the scaffold 114 below the epidermis 105 of the incisional wound 104 may facilitate closure of the incisional opening 103 of the incisional wound 104 and help maintain the reduced-pressure within the incisional wound 104 for a longer period of time Referring back to FIG. 2, in an alternative embodiment (not shown) the upper edge portion 124 of the scaffold 114 may protrude out of the incisional opening 103 above the epidermis 105 so that the sutures 130 may be stitched through the upper portion of the scaffold 114 to hold it firmly in place within the incisional wound 104. In this embodiment, the sutures 130 may be stitched sufficiently tight to substantially close the incisional opening 103 of the wound to further facilitate healing as described above.

Figure 4:
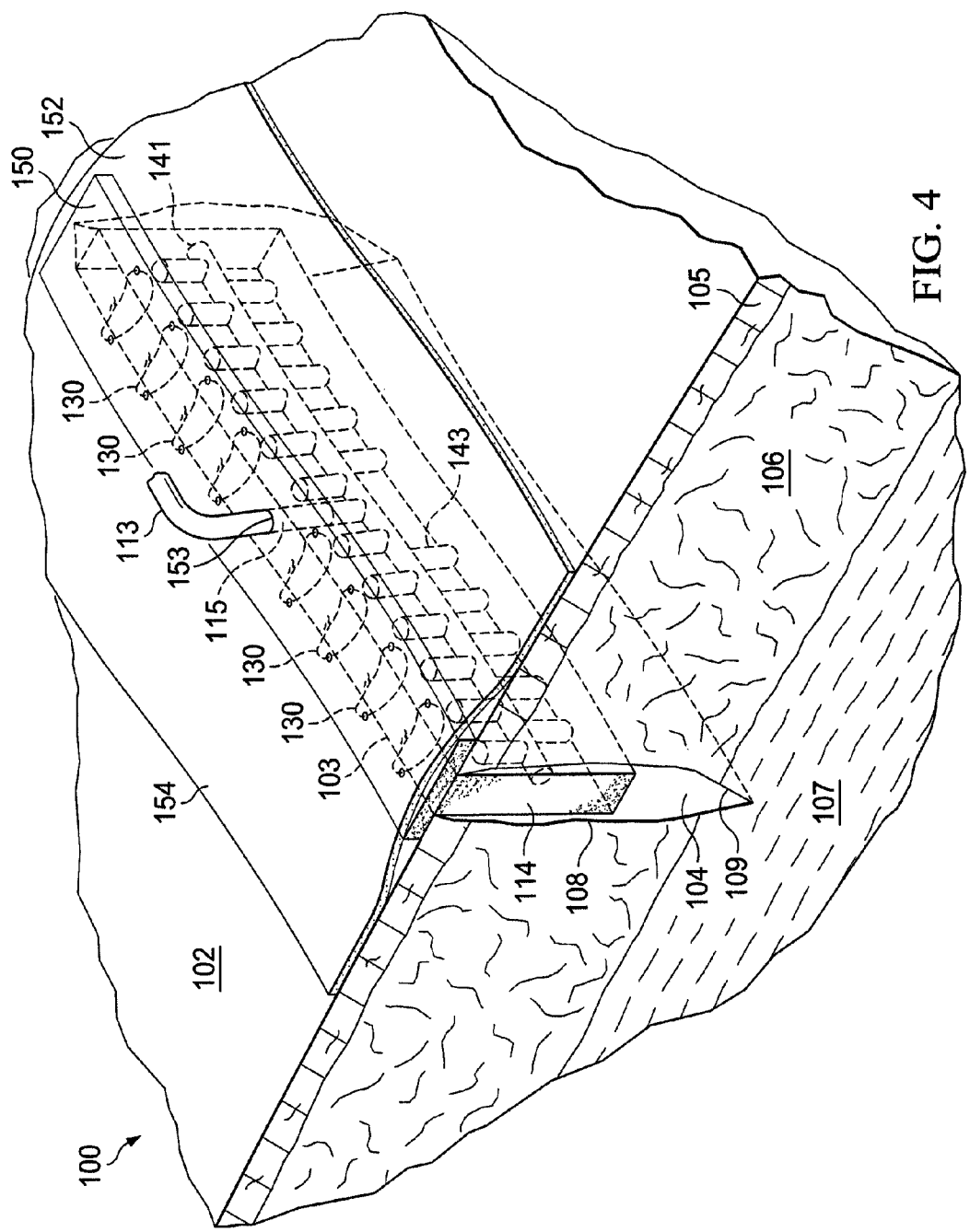
FIG. 4 is a schematic, cross-sectional, perspective view of an incisional wound and the scaffold shown in FIG. 2 including a drape covering the incisional wound.

In another embodiment shown in FIG. 4, the scaffold 114 may be exposed through the incisional opening 103 in the epidermis 105 as opposed to being closed within the incisional wound 104. In this embodiment, the system 100 may further comprise an external manifold 150 in fluid communication with the scaffold 114 and a drape 152 covering the external manifold 150 to maintain reduced pressure beneath the drape 152 within the incisional wound 104. The drape 152 includes an aperture 153 through which the conduit connector 115 extends to provide fluid communication between the second conduit 113 and the external manifold 150. The drape 152 may also include a periphery portion 154 that extends beyond the incisional opening 103 and includes an adhesive or bonding agent (not shown) to secure the drape 152 to the healthy tissue adjacent the incisional opening 103. The adhesive provides a seal between the drape 152 and the epidermis 105 to better maintain reduced pressure within the incisional wound 104. In another embodiment, a seal layer (not shown) such as, for example, a hydrogel or other material, may be disposed between the drape 152 and the epidermis 105 to augment or substitute for the sealing properties of the adhesive. The drape 152 may also be used in conjunction with the embodiments shown in FIGS. 2 and 3 described above.

The drape 152 may be any material that provides a pneumatic or fluid seal. The drape 152 may, for example, be an impermeable or semi-permeable, elastomeric material. As stated above, the drape 152 may include an adhesive layer on the periphery portion 154.

In view of the above, it will be seen that the advantages of the invention are achieved and other advantages attained. As various changes could be made in the above methods and compositions without departing from the scope of the invention, it is intended that all matter contained in the above description and shown in the accompanying drawings shall be interpreted as illustrative and not in a limiting sense.

It will be understood that the benefits and advantages described above may relate to one embodiment or may relate to several embodiments. It will further be understood that reference to "an" item refers to one or more of those items.

Where appropriate, aspects of any of the examples and embodiments described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of this invention.

We claim:

1. An apparatus for treating an incisional wound having incisional walls, the apparatus comprising:
   a conduit having a first end for receiving reduced pressure and a second end;
   a scaffold having opposing surfaces for positioning adjacent the incisional walls and fluidly coupled to the second end of said conduit for receiving the reduced pressure, said scaffold being generally elongated in shape and having a thickness between the opposing surfaces sufficiently thin for positioning within the incisional wound; and
   an internal manifold having a primary flow channel extending generally longitudinally within said scaffold between the opposing surfaces and fluidly coupled to the second end of said conduit, wherein the primary flow channel is formed by a bioresorbable tubing;

whereby application of the reduced pressure through said scaffold and said internal manifold induces tissue apposition between the incisional walls.

2. The apparatus of claim 1, wherein the internal manifold further comprises tributary flow channels fluidly coupled to the primary flow channel and extending generally transversely within said scaffold between the opposing surfaces.

3. The apparatus of claim 2, wherein the tributary flow channels extend generally perpendicular from the primary flow channel.

4. The apparatus of claim 2, wherein one or more of the tributary flow channels originate from a single location within the primary flow channel.

5. The apparatus of claim 1, wherein the primary flow channel is an anisotropic property of said scaffold.

6. The apparatus of claim 1, wherein the primary flow channel is formed by an alignment of interconnected pores of said scaffold.

7. The apparatus of claim 1, wherein the thickness of said scaffold is less than about 3.0 mm.

8. The apparatus of claim 1, wherein the thickness of said scaffold is greater than about 0.25 mm.

9. The apparatus of claim 1, wherein a ratio of a length to the thickness of said scaffold is greater than about 10.

10. The apparatus of claim 1, wherein said scaffold further comprises an edge portion configured not to be in contact with the incisional walls and an external manifold in fluid communication with the edge portion and fluidly coupled to the second end of said conduit.

11. The apparatus of claim 10, wherein said external manifold is positioned outside the incisional wound.

12. The apparatus of claim 1, wherein the scaffold is bioresorbable.

13. The apparatus of claim 1, wherein the scaffold is formed from polylactide-co-glycolide.

14. The apparatus of claim 1, wherein said scaffold is formed from resorbable polyurethane.

15. The apparatus of claim 1, wherein said scaffold is formed from decellularized biological material.

16. The apparatus of claim 1, wherein the scaffold is formed from collagen.

17. The apparatus of claim 1, wherein the scaffold is a reticulated structure.

18. The apparatus of claim 1, further comprising: an external manifold in fluid communication with a portion of the scaffold; and a drape formed of substantially impermeable material to cover said external manifold and said scaffold within the incisional wound.

19. A system for treating an incisional wound having incisional walls, the system comprising:
a pressure source to supply reduced pressure;
a conduit fluidly coupled to the pressure source having a first end for receiving the reduced pressure and a second end;
a scaffold fluidly coupled to the second end of said conduit for receiving the reduced pressure and having a length, a width, and a thickness defined by opposing surfaces for positioning within the incisional wound adjacent the incisional walls, said scaffold being formed from a porous material generally elongated in shape for positioning within the incisional wound the thickness being less than the length and the width; and
an internal manifold having a primary flow channel extending generally longitudinally within said scaffold between the opposing surfaces and fluidly coupled to the second end of said conduit, wherein the primary flow channel is formed by an alignment of interconnected pores of said scaffold;

whereby application of the reduced pressure through said scaffold and said internal manifold induces tissue apposition between the incisional walls.

20. The system of claim 19, wherein the internal manifold comprises tributary flow channels fluidly coupled to the primary flow channel and extending generally transversely within said scaffold between the opposing surfaces.

21. The system of claim 20, wherein the tributary flow channels extend generally perpendicular from the primary flow channel.

22. The system of claim 19, wherein one or more of the tributary flow channels originate from a single location within the primary flow channel.

23. The system of claim 19, wherein the primary flow channel is an anisotropic property of said scaffold.

24. The system of claim 19, wherein the primary flow channel is formed by bioresorbable tubing.

25. The system of claim 19, wherein said scaffold further comprises an edge portion configured not to be in contact with the incisional walls and an external manifold structure in fluid communication with the edge portion and fluidly coupled to the second end of said conduit.

26. The system of claim 25, wherein the incisional wound has an opening between the incisional walls and the edge portion is exposed through the opening.

27. The system of claim 26, wherein said external manifold is positioned outside the incisional wound.

28. The system of claim 19, wherein the incisional wound has an opening between the incisional walls and further comprises means for substantially closing the opening.

29. The system of claim 19, further comprising:
an external manifold in fluid communication with a portion of the scaffold; and
a drape formed of substantially impermeable material to cover said external manifold and said scaffold within the incisional wound.

30. The system of claim 19, further comprising a fluid source fluidly connected to the scaffold.

31. A system for treating an incisional wound having incisional walls, the system comprising:
a pressure source to supply reduced pressure;
a conduit fluidly coupled to the pressure source having a first end for receiving the reduced pressure and a second end;
a scaffold fluidly coupled to the second end of said conduit for receiving the reduced pressure and having opposing surfaces for positioning within the incisional wound adjacent the incisional walls, said scaffold being formed from a porous material generally elongated in shape for positioning within the incisional wound, said scaffold having a thickness greater than about 0.25 mm and less than about 3.0 mm; and
an internal manifold comprising:
a primary flow channel extending generally longitudinally within said scaffold between the opposing surfaces and fluidly coupled to the second end of said conduit, wherein the primary flow channel is formed by bioresorbable tubing; and
tributary flow channels fluidly coupled to the primary flow channel and extending generally transversely within said scaffold between the opposing surfaces, the tributary flow channels extending generally perpendicular from the primary flow channel;

whereby application of the reduced pressure through said scaffold and said internal manifold induces tissue apposition between the incisional walls.

32. The system of claim 31, further comprising:
an external manifold in fluid communication with a portion of the scaffold; and
a drape formed of substantially impermeable material to cover said external manifold and said scaffold within the incisional wound.

33. An apparatus for treating an incisional wound having incisional walls, the apparatus comprising:
a scaffold having a length, a width, and opposing surfaces for positioning adjacent the incisional walls, said scaffold being generally elongated in shape and having a thickness between the opposing surfaces that is less than the length and the width and is sufficiently thin for positioning within the incisional wound;
an internal manifold having a primary flow channel extending generally longitudinally within said scaffold between the opposing surfaces for fluidly coupling to a reduced pressure source;
an external manifold in fluid communication with a portion of the scaffold; and
a drape formed of substantially impermeable material to cover said external manifold and said scaffold within the incisional wound.

34. The apparatus of claim 33, wherein the internal manifold further comprises tributary flow channels fluidly coupled to the primary flow channel and extending generally transversely within said scaffold between the opposing surfaces.

35. The apparatus of claim 34, wherein the tributary flow channels extend generally perpendicular from the primary flow channel.

36. The apparatus of claim 34, wherein one or more of the tributary flow channels originate from a single location within the primary flow channel.

37. The apparatus of any of claims 33 to 36, wherein the primary flow channel is an anisotropic property of said scaffold.

38. The apparatus of any of claims 33 to 36 and 37, wherein the primary flow channel is formed by bioresorbable tubing.

39. The apparatus of any of claims 33 to 36, 37 and 38, wherein the primary flow channel is formed by an alignment of interconnected pores of said scaffold.

40. The apparatus of any of claims 33 to 36 and 37 to 39, wherein the thickness of said scaffold is less than about 3.0 mm.

41. The apparatus of any of claims 33 to 36 and 37 to 40, wherein the thickness of said scaffold is greater than about 0.25 mm.

42. The apparatus of any of claims 33 to 36 and 37 to 41, wherein a ratio of a length to the thickness of, said scaffold is greater than about 10.

43. The apparatus of any of claims 33 to 36 and 37 to 42, wherein said scaffold further comprises an edge portion configured not to be in contact with the incisional walls and an external manifold in fluid communication with the edge portion and fluidly coupled to the second end of said conduit.

44. The apparatus of claim 43, wherein said external manifold is positioned outside the incisional wound.

45. The apparatus of any of claims 33 to 36 and 37 to 44, wherein the scaffold is bioresorbable.

46. The apparatus of any of claims 33 to 36 and 37 to 45, wherein the scaffold is formed from polylactide-co-glycolide.

47. The apparatus of claim 46, wherein said scaffold is formed from resorbable polyurethane.

48. The apparatus of claim 47, wherein said scaffold is formed from decellularized biological material.

49. The apparatus of any of claims 33 to 36 and 37 to 48, wherein the scaffold is formed from collagen.

50. The apparatus of any of claims 33 to 36 and 37 to 49, wherein the scaffold is a reticulated structure.

51. The apparatus of any of claims 33 to 36 and 37 to 50, further comprising a conduit for fluidly coupling to the primary flow channel.

52. The apparatus of claim 51, further comprising a reduced pressure source fluidly coupled to the conduit.

53. An apparatus for treating an incisional wound having incisional walls, the apparatus comprising:
a conduit having a first end for receiving reduced pressure and a second end;
a scaffold having a length, a width, and opposing surfaces for positioning adjacent the incisional walls and fluidly coupled to the second end of said conduit for receiving the reduced pressure, said scaffold being generally elongated in shape and having a thickness between the opposing surfaces that is less than the length and the width and is sufficiently thin for positioning within the incisional wound; and
an internal manifold having a primary flow channel extending generally longitudinally within said scaffold between the opposing surfaces and fluidly coupled to the second end of said conduit, wherein the primary flow channel is formed by an alignment of interconnected pores of said scaffold;
whereby application of the reduced pressure through said scaffold and said internal manifold induces tissue apposition between the incisional walls.

54. An apparatus for treating an incisional wound having incisional walls, the apparatus comprising:
a scaffold having opposing surfaces for positioning adjacent the incisional walls, said scaffold being generally elongated in shape and having a thickness between the opposing surfaces sufficiently thin for positioning within the incisional wound; and
an internal manifold having a primary flow channel extending generally longitudinally within said scaffold between the opposing surfaces for fluidly coupling to a reduced pressure source, wherein the primary flow channel is formed by bioresorbable tubing.

55. An apparatus for treating an incisional wound having incisional walls, the apparatus comprising:
a scaffold having a length, a width, and opposing surfaces for positioning adjacent the incisional walls, said scaffold being generally elongated in shape and having a thickness between the opposing surfaces that is less than the length and the width and is sufficiently thin for positioning within the incisional wound; and
an internal manifold having a primary flow channel extending generally longitudinally within said scaffold between the opposing surfaces for fluidly coupling to a reduced pressure source, wherein the primary flow channel is formed by an alignment of interconnected pores of said scaffold.

* * * * *